(12) United States Patent
Eulgem et al.

(10) Patent No.: US 9,023,759 B2
(45) Date of Patent: May 5, 2015

(54) MOLECULES THAT INDUCE DISEASE RESISTANCE AND IMPROVE GROWTH IN PLANTS

(71) Applicant: The Regents of the University of California, Oakland, CA (US)

(72) Inventors: Thomas Eulgem, Riverside, CA (US); Melinda Rodriguez-Salus, Milwaukee, WI (US); Colleen M. Knoth, Costa Mesa, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/205,134

(22) Filed: Mar. 11, 2014

(65) Prior Publication Data

US 2014/0274700 A1     Sep. 18, 2014

Related U.S. Application Data

(60) Provisional application No. 61/777,931, filed on Mar. 12, 2013.

(51) Int. Cl.
  *A01N 25/26* (2006.01)
  *A01N 43/78* (2006.01)
  *C07D 277/56* (2006.01)

(52) U.S. Cl.
  CPC .............. *A01N 43/78* (2013.01); *C07D 277/56* (2013.01)

(58) Field of Classification Search
  None
  See application file for complete search history.

(56) References Cited

U.S. PATENT DOCUMENTS

2012/0329842 A1*   12/2012   Song et al. .................... 514/365

* cited by examiner

*Primary Examiner* — Alton Pryor
(74) *Attorney, Agent, or Firm* — Kilpatrick Townsend and Stockton LLP

(57) ABSTRACT

Described herein are methods and compositions for enhancing pathogen immunity in plants and improving plant growth.

20 Claims, 7 Drawing Sheets

MOLECULES THAT INDUCE DISEASE RESISTANCE AND IMPROVE GROWTH IN PLANTS

CROSS-REFERENCE TO RELATED APPLICATIONS

This application claims priority to U.S. Provisional Appl. No. 61/777,931 filed Mar. 12, 2013, the disclosure of which is incorporated by reference herein in its entirety.

STATEMENT AS TO RIGHTS TO INVENTIONS MADE UNDER FEDERALLY SPONSORED RESEARCH AND DEVELOPMENT

This invention was made with Government support under Grant Nos. DGE0504249 and IOB0449439 awarded by the National Science Foundation. The Government has certain rights in this invention.

BACKGROUND OF THE INVENTION

Plant innate immunity against pathogens depends on a network of functionally interconnected genes involved in the regulation and execution of defense reactions (Glazebrook et al. (2003) *Plant J.* 34:217; Tsuda et al. (2009) *PLoS Genet.* 5:e1000772). A fundamental form of innate immunity in plants involves conserved microbe-associated molecular patterns (MAMPs) or general elicitors. MAMPs are recognized by pattern recognition receptors (PRRs) on the surface of plant cells. Upon pathogen recognition, PRRs activate a comprehensive set of defense reactions collectively referred to as pattern triggered immunity (PTI). Some pathogens have independently acquired the ability to evade PTI through the release of effector molecules, suppressing defense and thus enabling infection (effector triggered susceptibility, ETS). In this case, the pathogen is virulent and the host susceptible. Even in the face of ETS, plants can mount a weakened immune response, called basal defense, which limits pathogen spread. Basal defense typically cannot fully prevent disease. As a countermeasure to ETS, plants have also evolved the ability to recognize the presence of effectors by highly specific plant resistance (R) proteins, which mediate effector triggered immunity (ETI) resulting in incompatible interactions and leaving pathogens avirulent.

ETI, basal defense, and PTI pathways share some signaling components, such as reactive oxygen species, $Ca^{2+}$, salicylic acid (SA) and jasmonic acid (JA) (Nimchuk et al. (2003) *Ann. Rev. Genet.* 37:579). The plant immune system can be subdivided into various defined sectors that can interact with each other. For example, distinct defense signaling sectors depend on early MAMP-activated MAP kinases or the messenger molecules SA or JA, and some of these sectors can interact in an additive or synergistic fashion during PTI, or in an antagonistic manner during ETI. The latter phenomenon can compensate if a defined sector is disabled due to interferences with a pathogen effector. A general review of chemical defense inducers can be found in Schreiber & Desveaux (2008) *Plant Pathology J.* 24:245.

Pesticides are commonly used in agriculture and horticulture for disease control. Current chemical pesticides, however, typically rely on direct antibiotic or biocidal activity, which often leads to undesirable toxic environmental side effects. For example, seven of the 10 most frequently used pesticides in California tomato production have potential acute toxic, carcinogenic, neurotoxic or groundwater-contaminating activities, or detrimental effects on human reproduction and development.

BRIEF SUMMARY OF THE INVENTION

Described herein is a class of synthetic elicitors for use in reduced-risk pathogen resistance. Without intending to limit the invention, it is believed that synthetic elicitors fight plant diseases by enhancing the plant's inherent defense system. We have surprisingly found that the compounds described herein enhance growth of root and aerial structures in plants, pointing to a multifunctional class of compounds for improved protection and growth of plants.

Provided herein is a class of multifunctional compounds having a 2-phenyl-thiazolidine-carboxylic acid (PTC) structure, including those of Formula I:

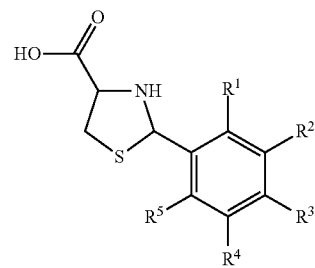

or a salt thereof, wherein:
$R^1$, $R^2$, $R^3$, $R^4$, and $R^5$ are each independently selected from hydrogen, halogen, hydroxyl, alkoxyl, and substituted (e.g., carboxyl substituted) or unsubstituted heterocycloalkyl (e.g., thiazolidine). Such compounds, when contacted with a plant, increase pathogen resistance or growth of the plant compared to pathogen resistance or growth of a control plant not contacted with the compound.

In some embodiments, $R^1$ is hydrogen or hydroxyl. In some embodiments, $R^2$ is hydrogen or bromo. In some embodiments, $R^3$ is hydrogen or $R^3$ is a carboxyl-substituted thiazolidine. In some embodiments, $R^4$ is hydrogen or bromo. In some embodiments, $R^5$ is hydrogen or methoxy. In some embodiments, $R^1$ is hydroxyl and $R^4$ is hydrogen or bromo. In some embodiments, $R^2$ is bromo and $R^4$ is hydrogen or methoxy. In some embodiments, the compound is selected from the group consisting of

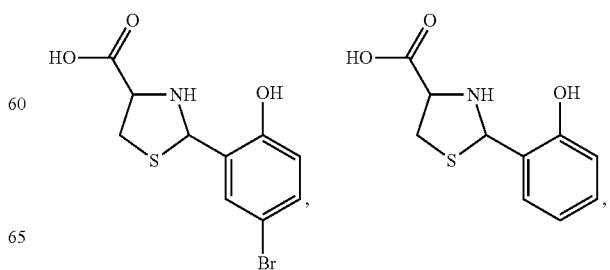

-continued

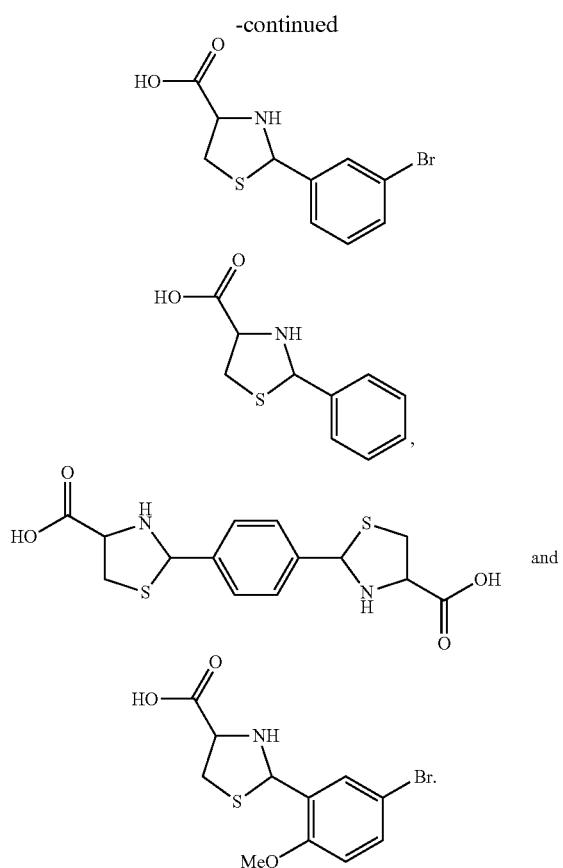

Further provided is an agricultural composition comprising the compound as described above formulated for application to a plant or plant part. In some embodiments, the agricultural composition also comprises at least one of an herbicide, an herbicide safener, a surfactant, a fungicide, a pesticide, a nematicide, a plant activator, a synergist, a plant growth regulator, an insect repellant, an acaricide, a molluscicide, or a fertilizer. In some embodiments, the agricultural composition is formulated for spraying or soaking. In some embodiments, the agricultural composition is formulated in a dry form, e.g., for dusting or soil application. In some embodiments, the agricultural composition is formulated in a dried or concentrated form to be rehydrated or diluted before application.

Further provided are methods of increasing pathogen resistance in a plant, comprising contacting (or applying to) the plant an effective amount of a compound as described above, e.g., in an agricultural composition, wherein the compound increases pathogen resistance in the plant compared to pathogen resistance in a plant not treated with the compound (e.g., an untreated control plant, or the same plant prior to contacting). In some embodiments, the compound increases pathogen resistance by at least 10, 20, 30, 40, 50, 60, 70, 80, 90, or 100% or more, e.g., as measured by increased pathogen response gene expression or by reduction in pathogen amount, number, or effect. In some embodiments, the compound reduces the amount or number of pathogen, or reduces the effect of pathogen, at least 1.5-fold, 2-fold, 3-fold, 5-fold, 10-fold or more. In some embodiments, the compound is applied at a concentration of 0.5-200 uM, 1-100 uM, 10-100 uM, 10 uM, 25 uM, 50 uM, 75 uM, or 100 uM. In some embodiments, the compound is applied more than once, e.g., at least 2, 3, 4, 5, 6, 7, 8, 9, or 10 times. In some embodiments, the compound is applied every 8 hours, twice daily, daily, every other day, twice weekly, etc. In some embodiments, the compound is contacted with a plant where the pathogen is already present. In some embodiments, the compound is contacted with a plant that is not affected by pathogen. In some embodiments, the method further comprises detecting the amount, number or effect of pathogen before contacting, and in some embodiments, further comprises detecting the amount, number or effect of pathogen after contacting one or more times. In some embodiments, the compound is contacted with the plant until the pathogen is not detectable, or is detectable at a level that does not affect the plant.

Further provided are methods of increasing growth of a plant, comprising contacting (or applying to) the plant an effective amount of a compound as described above, e.g., in an agricultural composition, wherein the compound increases growth of the plant compared to growth of a plant not treated with the compound (e.g., an untreated control plant grown in similar conditions). In some embodiments, the compound increases growth by at least 10, 20, 30, 40, 50, 60, 70, 80, 90, or 100% or more, e.g., as measured by size or weight of a plant structure. In some embodiments, the compound is applied at a concentration of 0.5-100 uM, 1-100 uM, 0.1-10 uM, 0.5-50 uM, 1 uM, 5 uM, 10 uM, 25 uM, 50 uM, 75 uM, or 100 uM. In some embodiments, the compound is applied more than once, e.g., at least 2, 3, 4, 5, 6, 7, 8, 9, or 10 times. In some embodiments, the compound is applied every 8 hours, twice daily, daily, every other day, twice weekly, etc. In some embodiments, the compound is contacted with a plant where pathogen is present.

DETAILED DESCRIPTION OF THE INVENTION

I. Introduction

Figure 1:
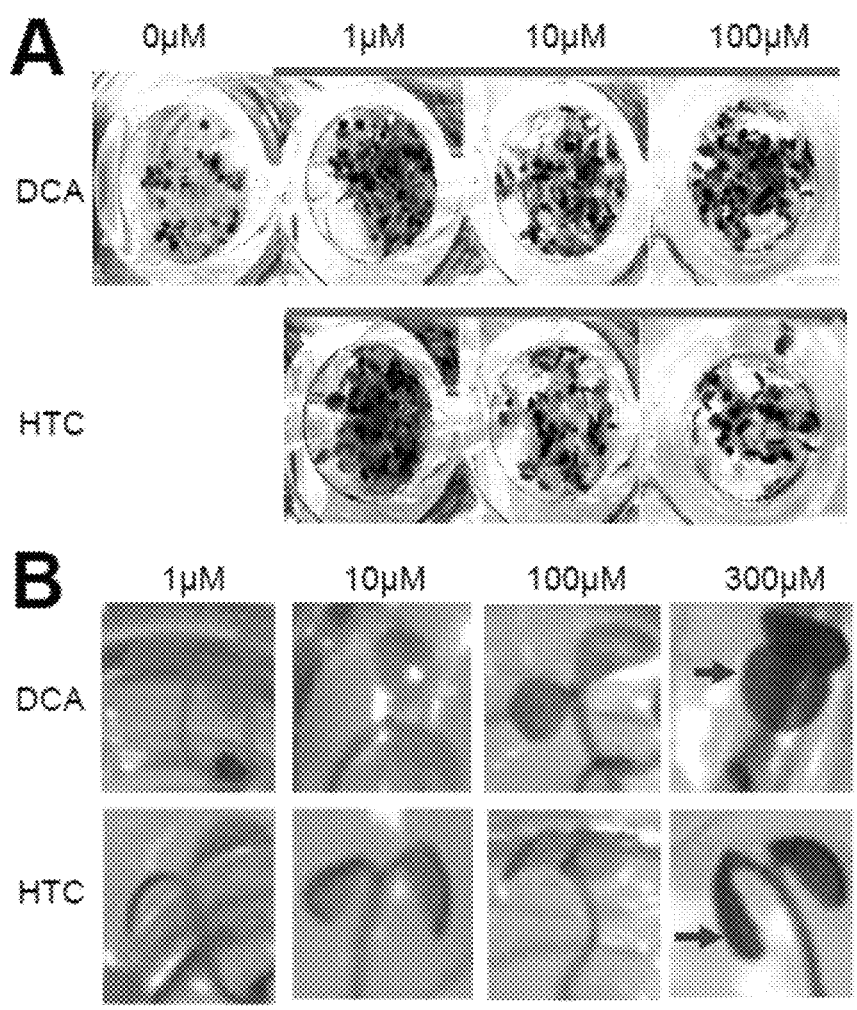
FIG. 1. Analysis of HTC activity under saturation treatment conditions. A. Screening plate containing 7d-old liquid-grown CaBP22$^{-333}$::GUS seedlings after x-gluc histochemical staining comparing reporter responses after 24 h incubation at indicated compound concentrations. The line above wells (1-100 uM) marks GUS stained seedlings. B. Trypan blue staining of CaBP22$^{-333}$::GUS seedlings incubated for 24 h in medium containing compounds at the indicated concentrations. Darkness of the cotyledons indicates cell death (toxicity) and is pointed to by arrows. The seed coats of seedlings are always darkly stained and can been seen in some images. All histochemical staining analyses were performed at least three times with similar results.

Synthetic elicitors are drug-like compounds that induce the plant natural immune response to pathogen. Synthetic elicitors need not be toxic for pathogenic organisms, which allows for production of a pathogen defense treatment that is less harmful to humans and the environment. Using high-throughput chemical screening, we identified synthetic elicitor candidates that activate expression of the pathogen-responsive CaBP22$^{-333}$::GUS reporter gene in transgenic *Arabidopsis thaliana* plants. One of these compounds, 2-(5-bromo-2-hydroxy-phenyl)-thiazolidine-4-carboxylic acid (HTC), is able to quickly and transiently induce disease resistance in *A. thaliana* and is structurally distinct from other known plant defense inducing chemicals. Surprisingly we found that HTC can enhance growth of roots and aerial parts of *A. thaliana* and tomato (*Solanum lycopersicum*). HTC beneficially affects both plant immunity and growth, thus providing a class of multi-functional agrochemicals. Moreover, several compounds that are structurally related to HTC (2-phenyl-thiazolidine-carboxylic acid (PTC) structures) are shown to have similar activity. Accordingly, provided herein is a class of structurally related compounds that can improve plant pathogen resistance and improve plant growth.

II. Definitions

An "agricultural composition" is a composition formulated for application to a plant or plant part (e.g., seed, cutting, shoots, etc.). An agricultural composition is typically in liquid form, e.g., for application by spraying or soaking, but can be in a powder for rehydration or application (dusting or dry coating), or gaseous form (e.g., for enclosed environments). The agricultural composition can be concentrated, e.g., for dilution or water or other solvent. An agricultural composition can also include more than one active ingredient, e.g., an HTC class compound in combination with a fungicide, herbicide, fertilizer, etc.

The terms "increase pathogen resistance," "enhance plant immunity," "promote disease resistance," "induce plant pathogen defense," "improve immunity to pathogens," and like terms refer to the ability of a substance to protect a plant from pathogen infection or infestation. The increase in protective effect is typically determined by comparison to a control. An agent or composition that increases pathogen resistance typically reduces the number/amount of pathogen affecting a plant at a given time post-infection by at least 1.5-fold, e.g., 2-fold, 3-fold, 5-fold, 10-fold, or more (or by 20%, 40%, 50%, 70%, 80%, 90% or more) compared to control not treated with the agent or composition. An increase in pathogen resistance can be measured in expression of pathogen-resistance genes (e.g., CaBP22, genes involved in salicylic acid synthesis, etc.) in an affected plant. An agent or composition that increases pathogen resistance can lead to an increase of a pathogen resistance gene by at least 1.5-fold, e.g., 2-fold, 3-fold, 5-fold, 10-fold, or more (or by 25%, 50%, 75%, 100% or more) compared to control not treated with the agent or composition. Pathogen resistance can also be determined by observing plant survival time, physical effects of pathogen invasion (e.g., lesions, stunted or abnormal growth, etc.). Thus, observing or quantifying plant health or the effects of pathogen on a plant can be determinative of the amount or number of pathogen present.

The terms "increase growth," "improve growth," "enhance growth," "promote growth," "induce growth," and like terms refer to the ability of a substance to speed up growth of a plant or plant structure over a given time span, typically as compared to a control. An agent or composition that increases growth typically increases the size or weight of a given plant structure, at a given time, by at least 10%, 20%, 40%, 50%, 70%, 80%, 90% or more compared to control not treated with the agent or composition.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a compound known to have the desired effect (positive control). A control can also represent an average value gathered from a number of tests or results. One of skill in the art will recognize that controls can be designed for assessment of any number of parameters. For example, a control can be devised to compare benefit, e.g., for peripheral composition considerations (e.g., half-life, adhesiveness) or for measures of the desired activity (e.g., comparison of pathogen resistance, growth, and/or side effects). Controls can be designed for in vitro applications, e.g., using reporter gene assays. One of skill in the art will understand which controls are valuable in a given situation and be able to analyze data based on comparisons to control values. Controls are also valuable for determining the significance of data. For example, if values for a given parameter vary in controls, variation in test samples will not be considered as significant.

Examples of negative controls in the context of the present disclosure include plants that are not treated with a particular composition, a plant before treatment, an average value of similar plants grown in similar but untreated conditions. Examples of positive controls include plants that are genetically modified for pathogen resistance or rapid growth, plants treated with a substance that is known to be toxic to the pathogen in question or known to increase pathogen resistance in a plant. One of skill in the art will understand how to select an appropriate control for a given condition.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec_butyl, tert_butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of $-(CH_2)_n-$, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Amine" refers to an $-N(R)_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen).

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo ($=$O), among many others.

The heterocycloalkyl groups can be at any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When a heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Heterocyclalkylene" refers to a heterocyclalkyl group, as defined above, linking at least two other groups. The two moieties linked to the heterocyclalkylene can be linked to the same atom or different atoms of the heterocyclalkylene. Heterocycloalkylene groups can be substituted or unsubstituted. As used herein, the term unsubstituted indicates the heterocycloalkyl has a full complement of hydrogens, i.e., commensurate with its saturation level, with no substitutions, e.g., linear decane (—$(CH_2)_9$—$CH_3$).

The term halide or halogen refers to the fluorine, chlorine, bromine, and iodine.

The term "hydroxyl" as used herein is represented by the formula —OH.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same. Plants that can be treated as described herein include angiosperms (monocotyledonous and dicotyledonous plants), gymnosperms, ferns, horsetails, psilophytes, lycophytes, bryophytes, and multicellular algae.

The term "plant" also includes naturally-occurring mutants, genetically-modified plants, and transgenic plants. A "genetically-modified plant" is one whose genome has been manipulated so that it is different than a wild-type plant of the same species, variety or cultivar, e.g., to add a gene or genetic element, remove a gene or genetic element, change chromatin structure, change RNA expression levels, etc. Genetically-modified plants include transgenic plants. A "transgenic plant" refers to a plant that contains genetic material not found in a wild-type plant of the same species, variety or cultivar. The genetic material can include a transgene, a reporter construct, an insertional mutagenesis event (such as by transposon or T-DNA insertional mutagenesis), an activation tagging sequence, a mutated sequence, a homologous recombination event or a sequence modified by chimeraplasty. A transgenic plant may contain an expression vector or cassette. The expression cassette typically comprises a polypeptide-encoding sequence or a modulating nucleic acid (e.g., an antisense, an siRNA or ribozyme) operably linked to (i.e., under regulatory control of) to an appropriate inducible or constitutive regulatory sequences that allow for the expression of a polypeptide or modulating nucleic acid. The expression cassette can be introduced into a plant by transformation or by breeding after transformation of a parent plant. Such methods can be used in a whole plant, including seedlings and mature plants, as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell. For example, in one embodiment, the disclosure provides an expression cassette comprising a pathogen response gene (e.g., CaBP22) promoter region operably linked to a heterologous polynucleotide, e.g., to determine if a given compound activates pathogen resistance pathways in a plant. The expression cassette can be used in an expression system, whereby induction of transcription by the promoter can be induced by contact with a compound of Formula I. Accordingly, transgenic plants comprising an expression cassette of the disclosure can be induced to express a desired gene or polynucleotide upon contact with a compound of Formula I.

III. Plants and Plant Pathogens

The presently described compounds can be effective for enhancing pathogen immunity and stimulating growth in a broad range of plants, e.g., dicots or monocots, and plants used for food, fiber, or energy production. Exemplary plant species include but are not limited to species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*. In some embodiments, the plant is an ornamental plant. In some embodiments, the plant is a vegetable- or fruit-producing plant, e.g., tomato, strawberry, fruit tree, etc. In some embodiments, the presently described compounds are applied to a plant selected from: apple, apricot, avocado, banana, blueberry, boysenberry, Brassicacea crop (e.g., cabbage, cauliflower, rape), carrot, citrus (e.g., orange, tangerine, lemon, grapefruit), cereal crop (e.g., rice, maize, wheat, barley, millet, sorghum, oats, triticale, rye), non-cereal grasses (e.g., bamboo, switch grass), cherry, date, fig, grape, kiwifruit, legume crop (e.g., bean, soybean, pea, cowpea, lentil), marijuana, nectarine, nut, olive, peach, pear, plum, raspberry, solanecea crop (e.g., tobacco, tomato, pepper, potato), strawberry, sugarbeet, sugarcane, and wood crops (e.g., birch, pine, poplar, oak, etc.).

Those of skill will recognize that a number of plant species can be used as models to predict the effects of the presently described compounds in other plants. For example, it is well recognized that tomato (*Solanum*) and *Arabidopsis* plants are useful models, e.g. for other dicots, and *Zea* can be a useful model for monocots in particular.

The presently described compounds enhance the immune response of the treated plant, and thus are believed to be effective against a variety of plant pathogens, e.g., bacteria, fungi, protists, and viruses. Exemplary pathogens include, but are not limited to, *Colletotrichum graminocola, Diplodia maydis, Verticillium dahliae, Fusarium graminearum, Fusarium oxysporum* and *Fusarium verticillioides*. The presently disclosed compounds can be used to address pathogens that affect major crops, including: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassuicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata, Glomerella glycines, Phakopsora pachyrhizi, Pythium aphanidermatum, Pythium ultimum, Pythium debaryanum, Fusarium solani*; Canola: *Albugo candida, Alternaria brassicae, Leptosphaeria maculans, Rhizoctonia solani, Sclerotinia sclerotiorum, Mycosphaerella brassicicola, Pythium ultimum, Hyeloperonospora arabidopsidis* (*Peronospora parasitica*), *Fusarium roseum, Alternaria alternata*; Alfalfa: *Clavibacter michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium albo-atrum, Xanthomonas campestris* p.v. *alfalfae, Aphanomyces euteiches, Stemphylium herbarum, Stemphylium alfalfae, Colletotrichum trifolii, Leptosphaerulina briosiana, Uromyces striates, Sclerotinia trifoliorum, Stagonospora meliloti, Stemphylium botryosum, Leptotrichila medicaginis*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondite* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana, Claviceps purpurea, Tilletia tritici, Tilletia laevis, Ustilago tritici, Tilletia indica, Rhizoctonia solani, Pythium arrhenomannes, Pythium gramicola, Pythium aphanidermatum*; Sunflower: *Plasmopora halstedii, Sclerotinia sclerotiorum, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Colletotrichum graminicola, Fusarium verticillioides* var. *subglutinans, Erwinia stewartii, F. verticillioides, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride, Claviceps sorghi, Pseudomonas avenae, Erwinia chrysanthemi* pv. *zea, Erwinia carotovora*, Corn stunt *spiroplasma, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*; Sorghum: *Exserohilum turcicum, C. sublineolum, Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinate, Fusarium verticillioides, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi, Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

IV. Compounds

A class of synthetic elicitors useful in the methods described herein includes compounds represented by Formula I:

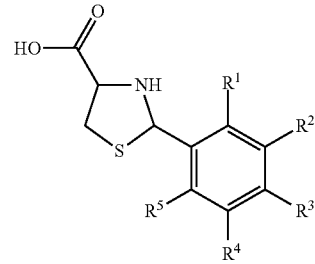

or a salt thereof.

In Formula I, $R^1$, $R^2$, $R^3$, $R^4$, and $R^5$ are each independently selected from hydrogen, halogen, hydroxyl, alkoxyl, amino, and substituted or unsubstituted heterocycloalkyl. Optionally, $R^1$ is hydrogen or hydroxyl. Optionally, $R^2$ is hydrogen or bromo. Optionally, $R^3$ is hydrogen or a substituted or unsubstituted heterocycloalkyl (e.g., a substituted thiazolidine, such as a carboxyl-substituted thiazolidine). Optionally, $R^4$ is hydrogen or bromo. Optionally, $R^5$ is hydrogen or methoxy.

Examples of Formula I include the following compounds:

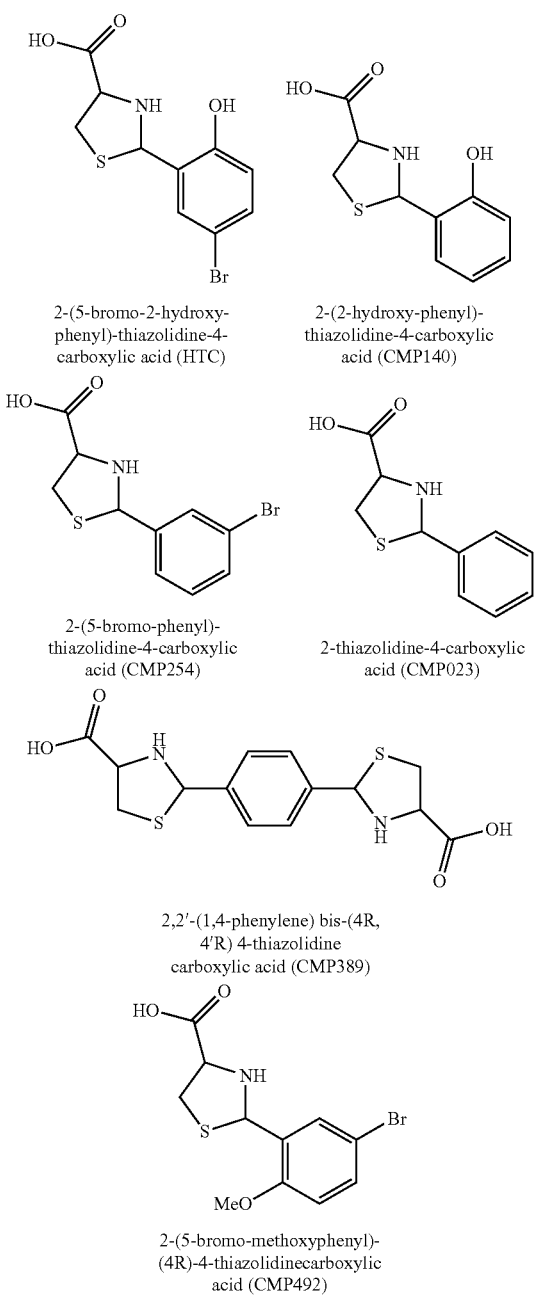

The compounds described herein include those with a 2-phenyl-thiazolidine-carboxylic acid (PTC) skeleton. In some cases, the compounds are commercially available (e.g., from Sigma-Aldrich®/TimTec®), or can be prepared using synthetic methods known in the art. The compounds described herein can be prepared from readily available starting materials. Optimum reaction conditions may vary with the particular reactants or solvent used, but such conditions can be determined by one skilled in the art by routine optimization procedures.

Variations on Formula I include the addition, subtraction, or movement of the various constituents as described for each compound. Similarly, when one or more chiral centers is present, the chirality of the molecule can be changed. Additionally, compound synthesis can involve the protection and deprotection of various chemical groups. The use of protection and deprotection, and the selection of appropriate protecting groups can be readily determined by one skilled in the art. The chemistry of protecting groups can be found, for example, in Wuts and Greene, Protective Groups in Organic Synthesis, 4$^{th}$ Ed., Wiley & Sons, 2006. Testing of synthesized compounds of Formula I can be carried out using reporter assays or pathogen protection assays, e.g., as described in the Examples.

Reactions to produce the compounds described herein can be carried out in one or more solvents, which can be readily selected by one of skill in the art of organic synthesis. Solvents can be substantially nonreactive with the starting materials (reactants), the intermediates, or products under the conditions at which the reactions are carried out, i.e., temperature and pressure. Product or intermediate formation can be monitored according to any suitable method, e.g., by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Compounds according to Formula I can be prepared, e.g., as described in Example 5, or according to Scheme 1.

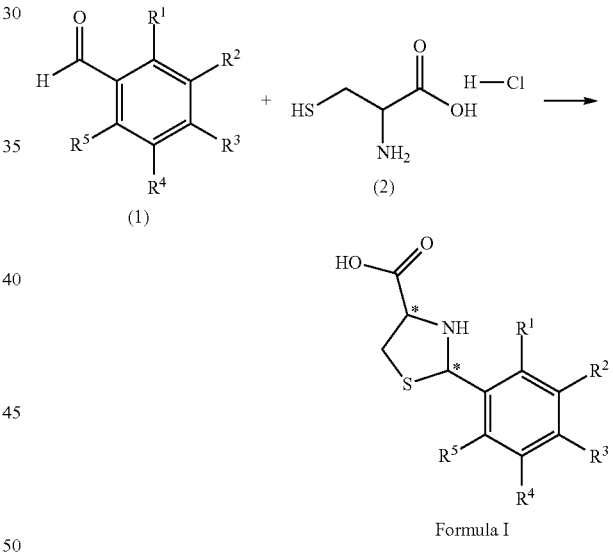

As shown in Scheme 1, the compound according to Formula I can be made, for example, by treating an aldehyde (1) with a cysteine hydrochloride (2) to form the compound according to Formula I. Optionally, the cysteine reagent can be a chiral molecule (e.g., L-cysteine hydrochloride) to form a compound of Formula I having chiral centers. Optional chiral centers in Formula I are indicated with asterisks in Scheme 1.

In some embodiments, the disclosure provides compositions for protecting a plant from a pathogen comprising an effective amount of at least one compound of Formula I (e.g., HTC, CMP140, CMP254, CMP023, CMP389, CMP492). In some embodiments, the application of the composition increases the expression of a plant pathogen responsive gene (e.g., CaBP22). "Effective amount" is intended to mean a compound or composition sufficient to reduce pathogen survival or growth, e.g., by 10%, 20%, 50%, 75%, 80%, 90%, 95%, or more compared to a negative control. In some embodiments, the effective amount of a compound of Formula I for protecting a plant from a pathogen is 0.05-250 uM, 0.1-200 uM, 0.1-100 uM, 0.5-100 uM, 10-100 uM, 0.5-50 uM, or 25-75 uM. A compound of the disclosure can be applied to a plant or plant part, e.g., the environment of the pathogen, by methods known to those of ordinary skill in the art, including those methods described herein.

In some embodiments, the disclosure provides compounds for increasing plant growth (e.g., roots, leaves, stems, etc.) comprising an effective amount of a compound of Formula I (e.g., HTC CMP140, CMP254, CMP023, CMP389, CMP492). "Effective amount" is intended to mean a compound or composition sufficient increase growth, e.g., by 10%, 20%, 50%, 75%, 80%, 90%, 100%, 150%, 200%, or more, compared to a negative control. In some embodiments, the effective amount of a compound of Formula I for increasing plant growth is 0.05-20 uM, 0.1-50 uM, 0.1-10 uM, 0.5-100 uM, 1-10 uM, 0.5-50 uM, or 0.1-1 uM. A compound of the disclosure can be applied to the plant or plant part by methods known to those of ordinary skill in the art, including those methods described herein.

V. Methods of Screening

Provided herein are methods to determine whether, and to what extent, an HTC-related compound (e.g., a compound of Formula I or a compound with a 2-phenyl-thiazolidine-carboxylic acid (PTC) skeleton) can be used to increase pathogen resistance or increase plant growth.

Assays for determining pathogen resistance are described herein, and include reporter assays, e.g., using a reporter construct comprising a regulatory region from a pathogen resistance gene (e.g. a gene on a salicylic acid-dependent pathway, or as described in Knoth et al. (2009) *Plant Physiol.* 150:333) operatively linked to a reporter (e.g., GFP, luciferase, or other detectable marker). Pathogen resistance can also be tested in situ, e.g., by contacting a plant with a pathogen in the presence or absence (negative control) of a test compound (e.g., an HTC-related compound, a compound of Formula I, or a compound with a 2-phenyl-thiazolidine-carboxylic acid (PTC) skeleton), and determining the pathogen protecting ability of the test compound by measuring the number or amount of the pathogen, or the effect of the pathogen on the plant (e.g., lesions, or reduced plant survival). The pathogen can be contacted with the plant at the same time, before, or after the test compound. In some embodiments, the plant is contacted with the test compound before and after contact with the pathogen. In some embodiments, the plant is contacted with the pathogen and/or test compound is contacted with the plant more than once, e.g., to determine the duration of efficacy of the compound. The assay can also include a positive control, e.g., a plant contacted with HTC. A reduced number, amount, or effect of pathogen compared to a negative control indicates the test compound increases pathogen resistance. One of skill will appreciate that methods of screening an HTC-related compound for its pathogen protecting activity can be adjusted, e.g., efficacy can be measured in different ways depending on the effect of the pathogen on the plant of interest. In addition, a plant tissue can be used instead of a whole plant. In some embodiments, the plant is a genetically-modified plant, e.g., a plant with a mutation in the SA-dependent pathogen signaling pathway (see, e.g., Lu (2009) *Plant Signal Behav.* 4:713), or as described in Example 4.

Similarly, assays for determining plant growth are described herein and known in the art. Growth can be measured from germination, in seedlings, in mature plants, in a plant tissue, or in plant cell culture. In some embodiments, the method comprises contacting a plant cell (e.g., in a plant part or whole plant) with a test compound (e.g., an HTC-related compound, a compound of Formula I or a compound with a 2-phenyl-thiazolidine-carboxylic acid (PTC) skeleton), and determining the growth rate of the plant cell compared to an untreated control. Growth rate can be determined by measuring the size or weight of a plant or plant part, or by determining the number of cells in a culture, at a given time after treatment. In some embodiments, the growth assay includes a positive control such as HTC.

VI. Agricultural Compositions

An agricultural composition comprising a compound of Formula I can also include one or more of: a surface-active agent, an inert carrier, a preservative, a humectant, a feeding stimulant, an attractant, an encapsulating agent, a binder, an emulsifier, a dye, a UV protective, a buffer, a flow agent, a fertilizer, a nitrogen fixation agent, micronutrient donors, or other preparations that influence plant growth. The agricultural composition can also include one or more agrochemicals including: herbicides, insecticides, fungicides, bactericides, nematicides, molluscicides, acaracides, plant growth regulators, harvest aids, and fertilizers, which can also be combined with carriers, surfactants or adjuvants as appropriate for the agrochemical. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present disclosure are normally applied in the form of compositions and can be applied to the crop area, plant, or seed to be treated. For example, the compositions of the present disclosure may be applied during growth, seeding or storage.

Surface-active agents that can be used with the presently described compounds include anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials that can be used with the presently described compounds include, but are not limited to, inorganic minerals such as kaolin, phyllosilicates, carbonates, sulfates, phosphates, or botanical materials such as cork, powdered corncobs, peanut hulls, rice hulls, and walnut shells.

Herbicides that can be used with the presently described compounds include compounds that kill or inhibit growth or replication of plants, typically a subset of plants that is distinct from the desired plant or crop. There are several modes of action: ACCase inhibition, carotenoid biosynthesis inhibition, cell wall synthesis inhibition, ALS inhibition, ESP synthase inhibition, glutamine synthase inhibition, HPPD inhibition, microtubule assembly inhibition, PPO inhibition, etc. Examples of commercially available herbicides include One-Time®, MSMA, Corvus®, Volunteer®, Escalade®, Q4®, Raptor®, Acumen®, Sencor®, Bullet®, TopNotch®, Valor®, PastureGard®, glycophosate (Roundup®), DSMA, Break-Up®, Hyvar®, Barricade®, etc. Herbicides can be mixed with "herbicide safeners" to reduce general toxicity of the herbicide, as described, e.g., in Riechers et al. (2010) *Plant Physiol.* 153:3.

Pesticides (e.g., nematicides, molluscicides, insecticides, miticide/acaricides) can be used in combination with the presently disclosed compounds to kill or reduce the population of undesirable pests affecting the plant. Pesticides can also be used with repellants or pheromones to disrupt mating behavior. Insectides are directed to insects, and include, e.g., those of botanical origin (e.g., allicin, nicotine, oxymatrine, jasmolin I and II, quassia, rhodojaponin III, and limonene), carbamate insecticides (e.g., carbaryl, carbofuran, carbosulfan, oxamyl, nitrilacarb, CPMC, EMPC, fenobucarb), fluorine insecticides, formamidine insecticides, fumigants (e.g., ethylene oxide, methyl bromide, carbon disulfide), chitin synthesis inhibitors, macrocyclic lactone insecticides, neonicotinoid insecticides, organophosphate insectides, urea and thiourea insectides, etc. Nematicides affect nematodes, and include, e.g., organophosphorus nematicides (e.g., diamidafos, fosthiazate, heterophos, phsphamidon, triazophos), fumigant nematicides (e.g., carbon disulfide, methyl bromide, methyl iodide), abamectin, carvacrol, carbamate nematicides (e.g., benomyl, oxamyl), etc. Molluscicides are directed to slugs and snails, and include, e.g., allicin, bromoacetamide, thiocarb, trifenmorph, fentin, copper sulfate, etc. Many pesticides target more than one type of pest, so that one or two can be selected to target insects, mollusks, nematodes, mitogens, etc.

Fertilizers typically provide macro- and micronutrients in a form that they can be utilized by the plant, or a plant-associated organism. These include, e.g., nitrogen, phosphorus, potassium, sulfur, calcium, potassium, boron, chlorine, copper, iron, manganese, molybdenum, zinc, nickel, and selenium. Fertilizers are often tailored to specific soil conditions or for particular crops or plants. Fertilizers that can be used with the presently described compounds include naturally-occurring, modified, concentrated and/or chemically synthesized materials, e.g., manure, bone meal, compost, fish meal, wood chips, etc., or can be chemically synthesized, UAN, anhydrous ammonium nitrate, urea, potash, etc. Suppliers include Scott®, SureCrop®, BCF®, RVR®, Gardenline®, and many others known in the art.

Fungicides are compounds that can kill fungi or inhibit fungal growth or replication. Fungicides that can be used with the presently disclosed compounds include contact, trans-laminar, and systemic fungicides. Examples include sulfur, neem oil, rosemary oil, jojoba, tea tree oil, *Bacillus subtilis*, Ulocladium, cinnamaldehyde, etc.

The compositions of the disclosure can be in a suitable form for direct application or as a concentrate of primary composition that requires dilution with a suitable quantity of water or other diluent before application. The concentration of a compound of Formula I will vary depending upon the nature of the particular formulation, specifically, whether it is a concentrate or to be used directly, the type of plant and pathogen, and in some cases, on the nature of the use, e.g., for plant growth or pathogen protection.

VII. Methods for Treating a Plant

The presently described compounds can be applied to the environment of a plant or plant pathogen by, for example, spraying, atomizing, dusting, scattering, coating or pouring, introducing into or on the soil, introducing into irrigation water, by seed treatment or general application or dusting at the time when the pathogen has begun to appear or before the appearance of pathogens as a protective measure. Typically pathogen control is contemplated early in plant growth, as this is the time when the plant can be most severely damaged. The compositions of the disclosure can conveniently contain an insecticide if this is thought necessary.

The presently described compounds can be applied simultaneously or in succession with other compounds. Methods of applying an active ingredient or agricultural composition of the present disclosure that contains at least one compound of Formula I include, but are not limited to, foliar application (e.g., spray or soak), seed coating, and soil application. The number of applications and the rate of application depend on desired use, e.g., pathogen protection or increased growth, and conditions, e.g., the intensity of pathogen infestation or growing conditions.

The examples and embodiments described herein are for illustrative purposes only, and various modifications or changes are to be included within the spirit and purview of this application and scope of the appended claims. All patents, patent applications, internet sources, and other published reference materials cited in this specification are incorporated herein by reference in their entireties.

VIII. Examples

A. Example 1

HTC is a Small Molecule Elicitor of CaBP22$^{-333}$::GUS Expression

We took a chemical genomics-based approach to identify new synthetic elicitors for the plant immune system and develop environmentally safe pesticides. By high-throughput chemical screening of commercially available chemical libraries, we identified drug-like organic compounds that induce the pathogen-responsive pCaBP22$^{-333}$::GUS reporter gene in transgenic *Arabidopsis*. We reported one of them, 3-5-dicholoroanthranlilic acid (DCA) in Knoth et al. (2009) *Plant Physiol.* 150:333. DCA triggered fast, strong and transient disease resistance against as the pathogenic oomycete *Hyaloperonospora arabidopsidis* (*Peronospora*) and the bacterial pathogen *Pseudomonas syringae*. DCA activity was shown in various *Arabidopsis* defense mutants to be partially dependent on the WRKY70 transcription factor, in contrast to INA and BTH, which are fully dependent on the transcriptional co-factor.

HTC was also selected from the compounds identified in the reporter assay screen. HTC was selected from the Sigma-Aldrich®/TimTec® MyriaScreen® library, but has not been reported as a synthetic elicitor, and has a chemical structure distinct from DCA or any other known plant defense inducer. To quantify the bioactivity of HTC, we performed various assays with one week-old CaBP22$^{-333}$::GUS seedlings submerged in liquid growth medium containing HTC or mock-solution (saturation treatment). HTC activated CaBP22$^{-333}$::GUS expression within 24 h at a concentration as low as 1 µM (FIG. 1A). To examine if HTC induces phytotoxicity, we stained Col-0 seedlings after saturation treatment with trypan blue. We observed dark staining indicating cell death in 100% of the seedlings treated for 24 h with 300 µM HTC (FIG. 1B). No cell death was observed at lower concentrations that resulted in reporter activation (1-100 µM), indicating that HTC-induced phytotoxicity is not responsible for its effect on CaBP22$^{-333}$::GUS expression.

B. Example 2

HTC Causes Rapid and Transient Resistance to *Peronospora*

We next tested whether HTC could induce pathogen resistance in soil-grown plants. Col-0 sprayed with HTC concentrations as low as 10 µM prior to infection with the virulent *Peronospora* isolate Noco2 exhibited significantly reduced numbers of Noco2 spores 7 days post infection (dpi). To determine if HTC differs from other synthetic elicitors in the kinetics of defense induction, Col-0 seedlings were sprayed with 100 µM of INA, DCA, HTC, or mock, 1 h, 3 h, 1 d, 3 d, or 6 d prior to pathogen challenge. The mock solvent treatment diminished spore growth when pathogen treatment and pre-treatment were less than one day apart, possibly due to liquid coating *Arabidopsis* seedlings and interfering with the *Peronospora* spore suspension.

Figure 2:
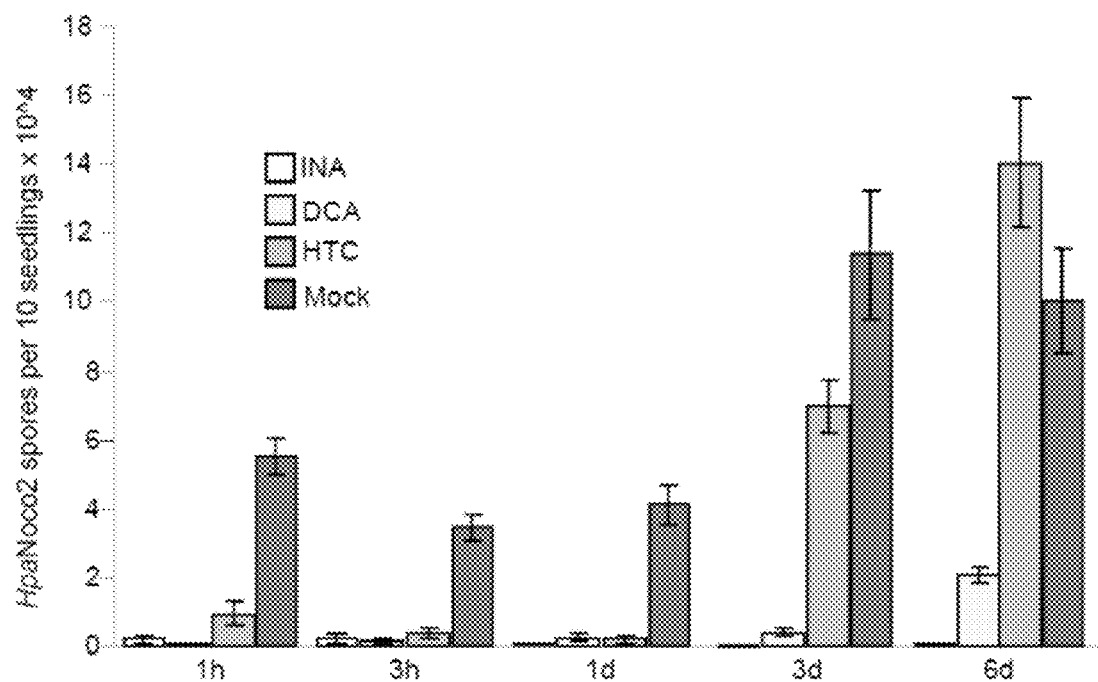
FIG. 2. Kinetic analysis of chemically-induced disease resistance. Experiments were conducted with three-week-old soil-grown Col-0 seedlings sprayed with 100 µM HTC, DCA, INA, or mock solution (1% DMSO) at the indicated times prior to being sprayed with 2×10$^4$ mL$^{-1}$ Noco2 spores (2 ml per pot). Peronospora (Hyeloperonospora arabidopsidis) spores were counted 7 dpi (days post-infection). Mean and SE values were calculated from a minimum of three biological replicates and the average of those is shown above. The Student's t-test (p<0.05) showed significant differences for all of the synthetic elicitor treatments relative to the mock-treated control, except for 6 dpt (days post-treatment) with HTC.

DCA and INA induced full resistance to Noco2 1 h post treatment (hpt). All three synthetic elicitors strongly suppressed *Peronospora* spore production to similar levels by 3 hpt. FIG. 2 shows that HTC-triggered immunity to Noco2 was reduced at 3 days post treatment (dpt), and not detectable at 6 dpt it was no longer detectable. The results show that HTC, like DCA, is a fast, potent, but reversible inducer of immunity against Noco2.

C. Example 3

Structure-Activity Analysis of HTC

Figure 3:
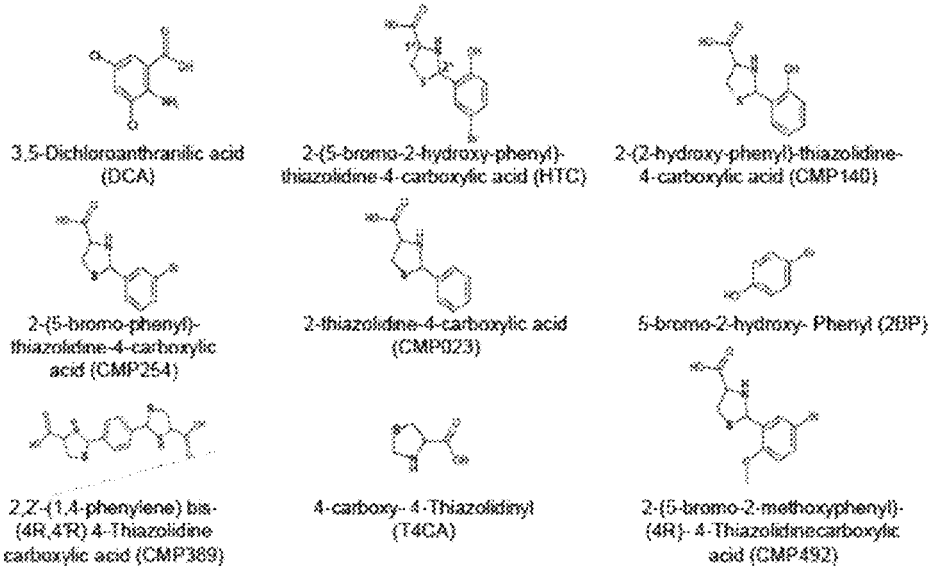
FIG. 3. Structure-activity analysis of HTC analogs. A. Chemical structures of DCA, HTC and tested HTC analogs. Chiral centers of the HTC skeleton are indicated by "1*" and "2*" in HTC. B. Noco2 spore inhibition assay. Three-week-old soil-grown Col-0 seedlings were spray-infected 24 h after treating with varying concentrations of each synthetic elicitor and then assayed at 7 dpi for spore growth. 100% inhibition=0 spores. The assay was repeated three times with similar results. The average of those three replicates is shown. Significant differences of compound-treated compared to mock-treated seedlings determined by Student's t-tests (p<0.05) are marked by colored four pointed stars.
Figure 3:
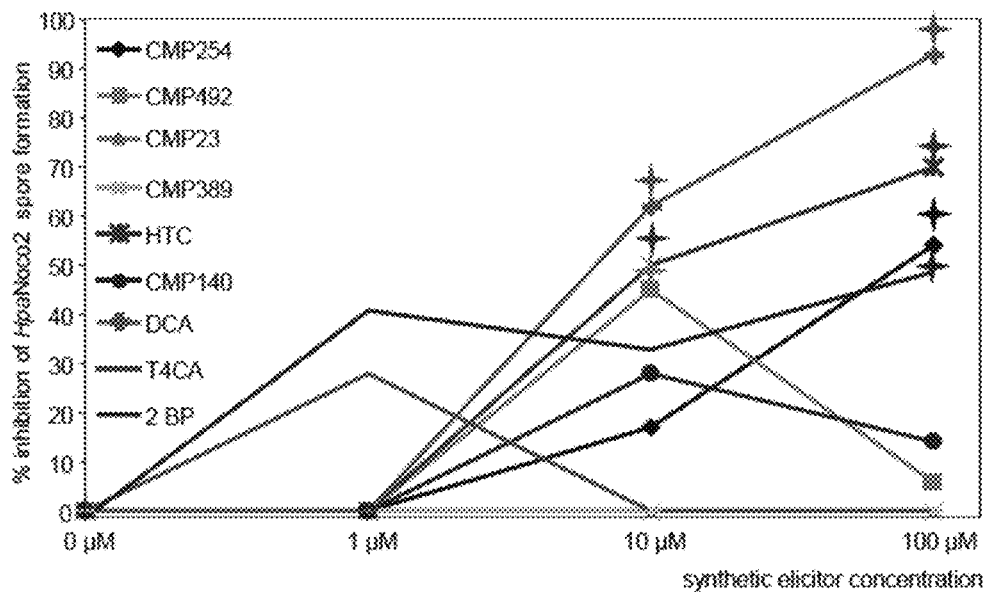

To determine which substituents or moieties of the HTC molecule are critical for its defense-inducing activity, seven commercially available HTC analogs were analyzed (FIG. 3A). We compared the ability of these compounds to induce GUS expression in saturation treated CaBP22$^{-333}$::GUS *Arabidopsis* seedlings to that of DCA and HTC. Except for 4-carboxy-4-thiazolidinyl (T4CA) and 5-bromo-2-hydroxy-phenyl (2BP), which represent the two halves of HTC when linked by a covalent bond, all tested HTC analogs induced CaBP22$^{-333}$::GUS expression at concentrations between 1-100 uM. The most efficient HTC analog was 2-(2-hydroxyphenyl)-thiazolidine-4-carboxylic acid (CMP140), which lacks the bromine substituent of the phenyl ring. We also used trypan blue staining to examine HTC-analog-induced phytotoxicity. Cell death, indicated by staining, was observed in 100% of the seedlings treated for 24 h at 300 µM of HTC and DCA. No cell death was observed at any concentrations examined for the HTC analogs, indicating that cell death was not responsible for CaBP22$^{-333}$::GUS activation by these compounds.

We performed a dose-response analysis of inhibition of Noco2 spore development in three-week old Col-0 plants using the HTC analogs (FIG. 3B). The data from the Noco2 defense assays and the reporter gene assays showed similar trends. DCA and HTC provided highest protection against Noco2 infection, significantly protecting Col-0 from *Peronospora* at 10 uM. T4CA and 2BP did not result in significant immunity, except for 2BP at 100 uM. CMP 140, which could induce CaBP22$^{-333}$::GUS expression, was a less efficient defense inducer compared to HTC, and a concentration of at least 100 uM was required to significantly reduce pathogen growth. All remaining compounds, which are all derivatives of the 2-phenyl-thiazolidine-carboxylic acid (PTC) skeleton exhibited intermediate levels of defense-inducing activity. The results show that HTC is the most potent of the tested analogs, but the fact that other PTC derivatives successfully activate immune responses establishes PTCs as a new class of synthetic elicitors.

D. Example 4

HTC is Functionally Distinct from DCA

Figure 4:
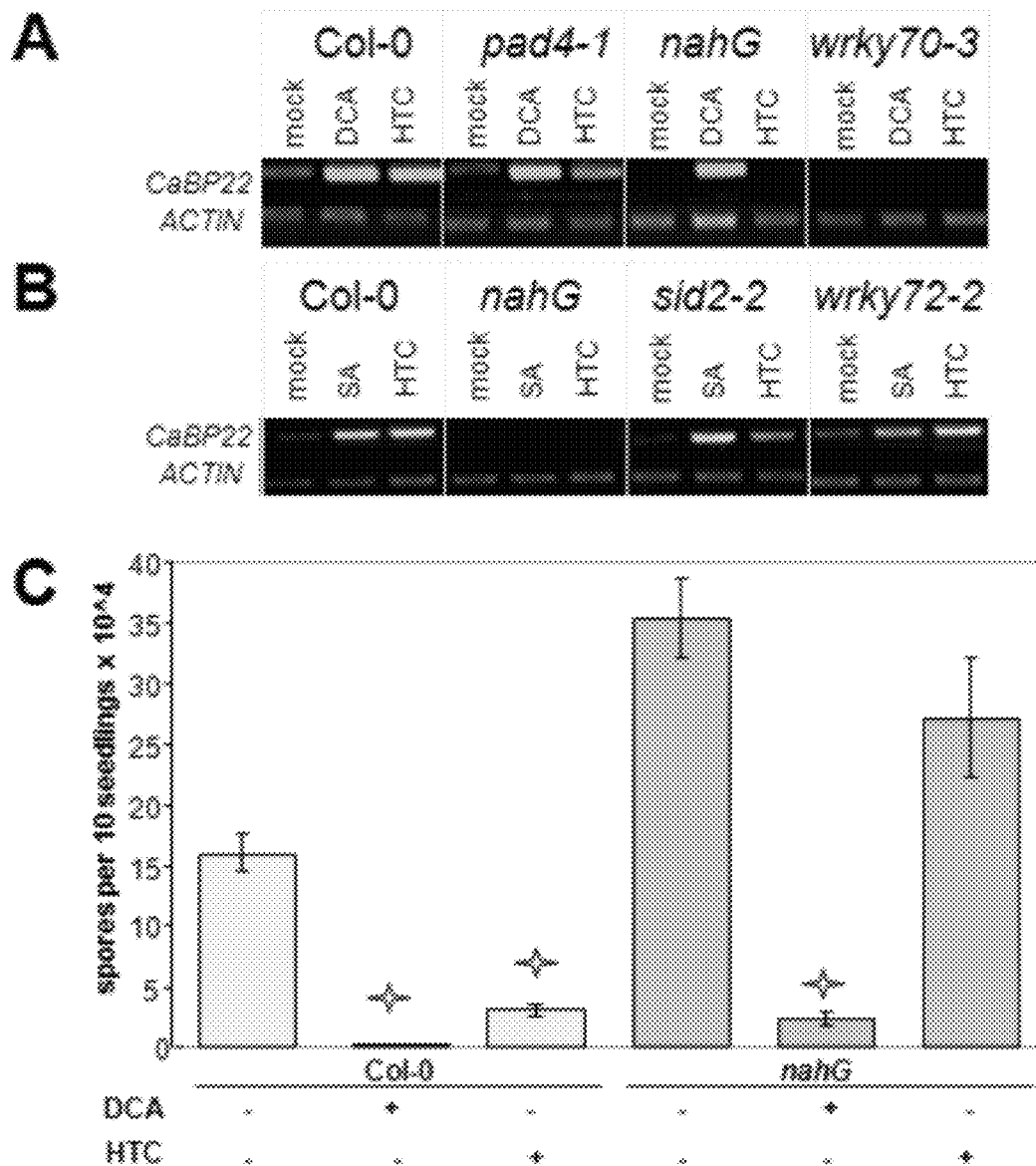
FIG. 4. Analysis of HTC activity in defense mutant plants. A & B. RT-PCR analysis of CaBP22 transcript levels in Col-0 (wild-type) and mutant backgrounds 24 h after spraying 2-week-old seedlings with mock-solution (1% DMSO), 100 µM DCA, or HTC. RT-PCRs with ACTIN are shown as loading controls. At least three biological replicates showed consistent results. C. Analysis of HTC activity in Col-0 or nahG background. Experiments were conducted with three-week-old soil-grown Col-0 or nahG seedlings sprayed with 100 µM HTC, 100 µM DCA, or mock-solution (1% DMSO) 24 h prior to infection with $2 \times 10^4$ virulent Noco2 spores $ml^{-1}$ (2 ml per pot). Spores were counted at 7 dpi. Mean and SE values were calculated from a minimum of three biological replicates and their averages of are shown. The Student's t-test (p<0.05) showed that HTC significantly suppresses Noco2 spore formation in Col-0 but not nahG, while DCA significantly suppresses Noco2 spore formation in both backgrounds (marked by stars).

To establish the mode-of-action of HTC, we performed reverse transcription (RT)-PCRs examining transcript levels of the defense marker gene CaBP22 in Col-0 and a set of mutant lines representing various defense signaling mechanisms. Both DCA and HTC induced an increase of CaBP22 transcript levels in Col-0 plants, but not in the wrky70-3 mutant (FIG. 4A). In the transgenic nahG line, which is compromised in the accumulation of salicylic acid (SA), the ability of HTC to induce CaBP22 expression was blocked, while that of DCA was not affected (FIGS. 4A and B).

These results show that the mode-of-action of HTC is distinct from that of DCA and that HTC likely interferes with defense signaling upstream of SA. Consistently, HTC-induced CaBP22 transcript accumulation is reduced in the pad4-1 and sid2-2 mutants, which are deficient in a distinct pathway of defense-associated SA synthesis (FIGS. 4A and B). The wrky72-2 mutant, which is likely be deficient in an SA-independent basal defense mechanism (Bhattarai et al. (2010) *Plant J.* 63:229), exhibits full HTC-induced CaBP22 transcript accumulation (FIG. 4B). Furthermore, DCA induced resistance to Noco2 in both Col-0 and nahG, while HTC was only able to do so in Col-0 (FIG. 4C). We did not observe significant reduction of Noco2 spores in nahG mutants after HTC treatment. These results confirm that the mode-of-action of HTC is distinct from that of DCA.

E. Example 5

Synthesis of HTC

Our studies were performed with HTC purchased from Sigma TimTec® (p-HTC). HTC can, however, be easily synthesized through the reaction of L-Cysteine hydrochloride with 5-bromo-salicylaldehyde. We synthesized HTC (s-HTC) using the protocols described in Kulaeva et al. (1992) *Plant Mol. Biol.* 20:383 and Song et al. (2009) *PNAS* 106:1654. Briefly, 2.0 g L-cysteine hydrochloride and 1.0 g NaOAc were dissolved in 17 mL sterile MilliQ® water. 1.0 g 5'bromo-salicylaldehyde dissolved in 18 mL was added to this solution with constant stirring. The mixture was vigorously stirred at room temperature overnight. The product was separated by suction filtration and washed several times with water and then ethanol.

The s-HTC preparation produced a nuclear magnetic resonance (NMR) spectrum identical to that obtained with p-HTC. We also compared the biological activity of s-HTC to that of p-HTC by spraying a concentration gradient of both preparations on soil-grown Col-0 seedlings 24 h prior to challenge with Noco2. No significant difference was found between the efficacy of s-HTC and p-HTC in reducing Noco2 spore counts at 20, 50, 100, and 200 µM. HTC has two chiral centers (indicated with 1* and 2* in FIG. 3A), but only two conformations of the diastereomers were detected by NMR. NMR analysis further revealed that these two diastereomers are present in s-HTC and p-HTC at the same ratio (40% to 60%).

F. Example 6

HTC Induces Growth of Plant Structures

Figure 5:
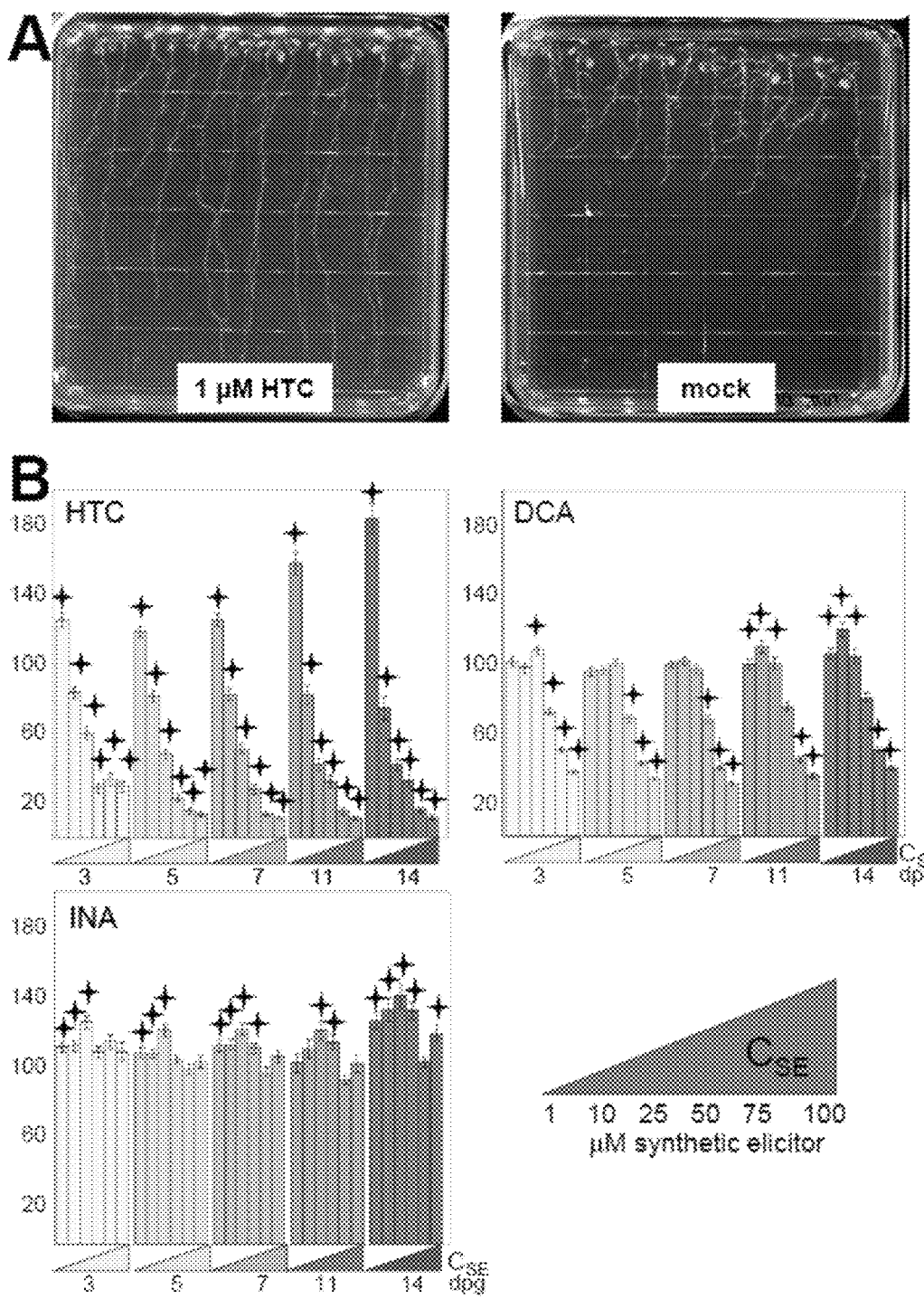
FIG. 5. Relative root length of Col-0 plants grown on synthetic elicitors. Col-0 seedlings were plated in square petri dishes on ½MS medium containing 1, 10, 25, 50, 75 or 100 µM of HTC, DCA, INA, or the respective controls (solvent only). A. Roots of Col-0 seedlings grown on 1 uM HTC or control (0.01% DMSO) medium 14 days after germination. B. Average percent Col-0 root length grown on synthetic elicitors compared to Col-0 grown on control. Root length was measured at day 3, 5, 7, 11, and 14. Results are expressed as percentages of the average root length on the respective synthetic elicitor treatments compared to their controls. The average, standard error, and Student's t-test (p<0.05) were calculated from these values. Significant differences between synthetic elicitor-treated and control-treated plants are marked by a star above the corresponding data point. Y-axis represents relative root growth in the presence of synthetic elicitor. $C_{SE}$: concentration of synthetic elicitor; dpg: days post germination.

Surprisingly, at low concentrations (1 µM) HTC enhanced the root length of *Arabidopsis* plants grown on ½MS agar plates (FIGS. 5A and B). As shown in FIG. 1A, this dose is sufficient to induce CaBP22$^{-333}$::GUS expression. Higher doses of HTC resulted in reduced root growth. We compared the ability of other synthetic elicitors to enhance growth, and performed root growth assays with INA, DCA, and HTC (FIG. 5B). Each synthetic elicitor was added to the solid media plates at concentrations ranging from 1 to 100 µM. The plates were placed upright in a growth chamber, and root lengths were measured at 3 d-intervals. To merge data sets, root length was expressed as a percentage of their value relative to the average of the mock (control) for that data set. Normalizing each root length to its control allowed all replicates to be combined together to calculate averages, standard errors, and perform statistical tests (FIG. 5B).

The effect was most dramatic with HTC, which at 1 µM increased root length to up to 180% of that observed on control plates, but DCA and INA also enhanced *Arabidopsis* root growth. HTC exhibited this root lengthening activity only at the lowest tested concentration (1 µM), in contrast to DCA and INA, which enhanced root length at various different tested concentrations. For all three tested synthetic elicitors, enhancement of root growth was detectable within three days of germination, but was more pronounced at later time-points. Both HTC and DCA, but not INA, strongly inhibited *Arabidopsis* root growth at higher concentrations. Again, this effect was most pronounced with HTC, which at concentrations above 50 µM reduced the length of *Arabidopsis* roots by ~80%. The observation that low doses of HTC and DCA stimulate root growth, while high doses inhibit root growth, is reminiscent of hormesis, a phenomenon characterized by low dose stimulation and high dose inhibition of biological responses.

Figure 6:
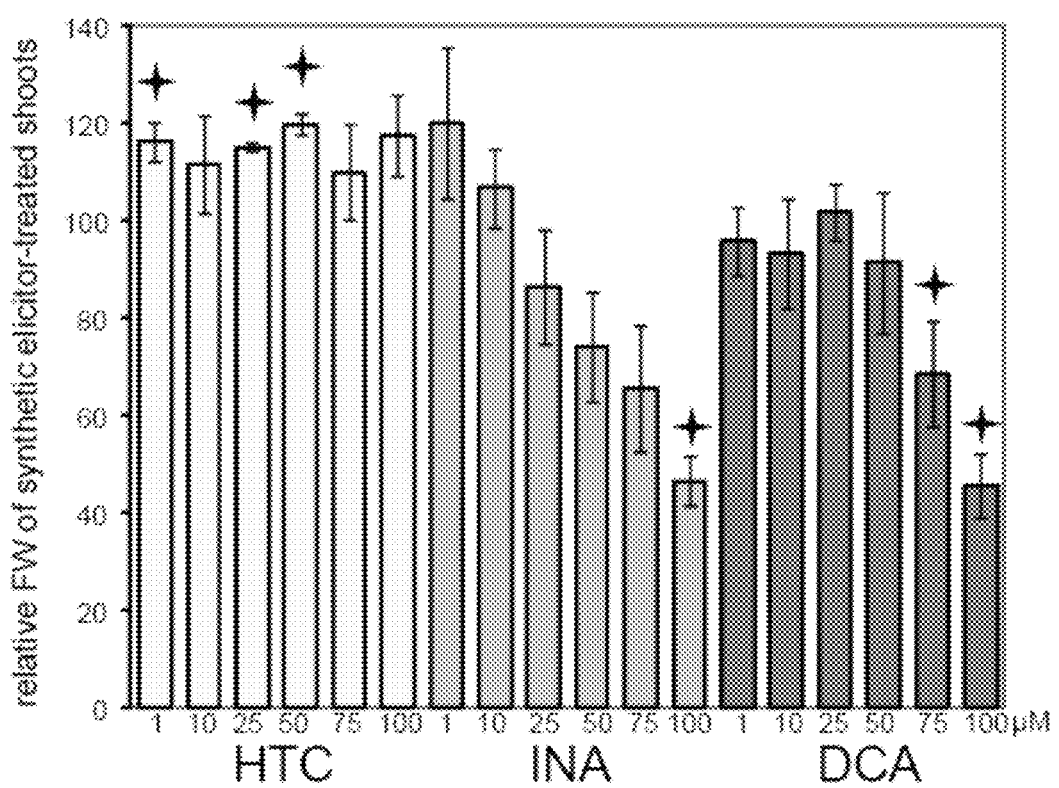
FIG. 6. Relative weight of aerial portions of synthetic elicitor treated Col-0 seedlings compared to control (DMSO) treated seedlings. Col-0 seeds (15-20 seeds per pot) were sown on soil drenched with 20 mL of the indicated concentrations of HTC, INA, DCA, or the respective mock solutions. Fresh weight (FW) of the above-ground plant tissues was measured at day 14. Results are expressed as percentages of the average FW of the respective synthetic elicitor treated plants compared to that of mock-treated controls. The standard error and Student's t-test (p<0.05) were calculated from at least three biological replicates and averages are shown. Significant differences between synthetic elicitor-treated and control-treated plants are marked by a star above the corresponding data point. Y-axis represents percent of FW in the presence of synthetic elicitor compared to controls.

To determine whether the synthetic inhibitors could increase the aerial weight of *Arabidopsis*, soil-sown-seedlings were drenched with synthetic elicitor in water at day 0 (FIG. 6). After 14 days, aerial portions of plants were cut off and their fresh weight measured. Shoots of plants treated with 1-100 µM HTC showed a significant increase in their fresh weight, reaching ~120% of the values observed with mock-treated plants. HTC thus has a hormesis-like effect in *Arabidopsis* roots, but generally increases the aerial fresh weight of *Arabidopsis* at the concentrations tested.

Figure 7:
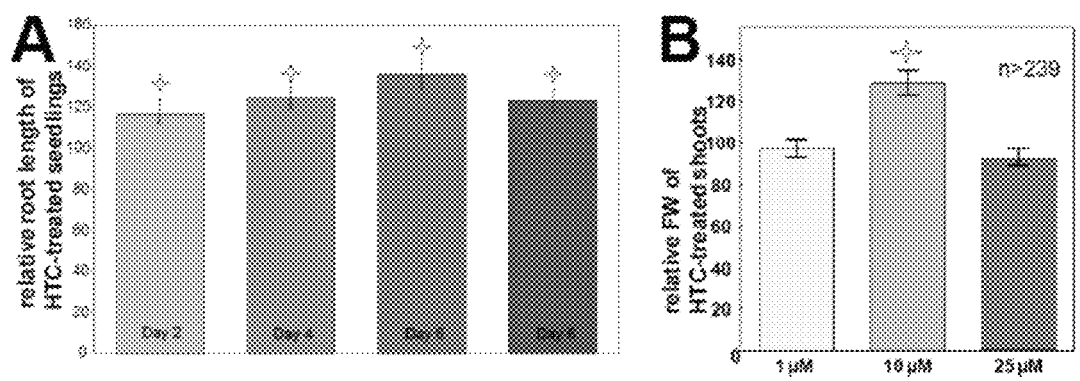
FIG. 7. Relative root length and FW of tomato seedlings and shoots. Tomato cv. Moneymaker seedlings treated with HTC compared to seedlings treated with control (DMSO 0.01%). A. Moneymaker seedlings were plated in square petri dishes on ½MS medium containing HTC. Root length was measured at day 2, 4, 6, and 8. Results are expressed as percentages of the average root length on 1 µM HTC or control. The average, standard error, and Student's t-test (p<0.05) were calculated from these values. Each time point represents at least 89 distinct root length measurements from at least three biological replicates. Y-axis represents percent of root growth in the presence of synthetic elicitor compared to controls. B. Moneymaker seeds (five seeds per pot with a minimum of 21 pots) were sown on soil drenched with 20 ml of the indicated concentrations of HTC or their respective control. Fresh weight (FW) of the above-ground plant tissues was measured at day 14. Results are expressed as percentages of the average weight of HTC treatments compared to those of the controls. The standard error and Student's t-test (p<0.01) were calculated from at least three biological replicates and the average is shown above. Significant differences between synthetic elicitor-treated and control-treated plants are marked by stars above the corresponding data points. Y-axis represents percent of weight in the presence of HTC compared to controls.

We also performed root and shoot growth assays with tomato plants. We applied 1 µM HTC to a large set of plate-grown tomato plants (n>89) resulted in a significant increase in root length at all analyzed time-points (FIG. 7A). The greatest increase was seen at day 6 with HTC-treated tomato reaching 136.1% of the root length of mock-treated plants. We also performed root drench-assays to determine effects of HTC on aerial plant mass in soil-grown tomato. Tomato seedlings were planted in soil and drenched a single time with 1, 10, or 25 µM of HTC (FIG. 7B). Application of 10 µM HTC caused a significant increase in the mass of shoots, resulting in 128.5% of the fresh weight measured in mock-treated plants. The data show that HTC causes an increase in both the root length and aerial weight of tomato plants.

What is claimed is:

1. An agricultural composition to be applied to plant or parts thereof comprising the compound of Formula I

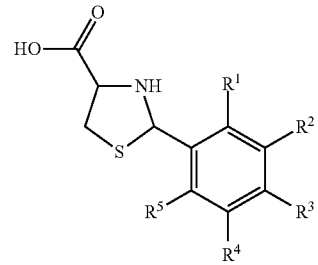

or a salt thereof, wherein:
$R^1$, $R^2$, $R^3$, $R^4$, and $R^5$ are each independently selected from hydrogen, halogen, hydroxyl, alkoxyl, and substituted or unsubstituted heterocycloalkyl,
wherein, when contacted with a plant, the compound increases pathogen resistance or growth of the plant or part thereof compared to pathogen resistance or growth of a control plant not contacted with the compound.

2. The agricultural composition of claim 1, wherein $R^1$ is hydrogen or hydroxyl.

3. The agricultural composition of claim 1, wherein $R^2$ is hydrogen or bromo.

4. The agricultural composition of claim 1, wherein $R^3$ is hydrogen.

5. The agricultural composition of claim 1, wherein $R^3$ is a carboxyl-substituted thiazolidine.

6. The agricultural composition of claim 1, wherein $R^4$ is hydrogen or bromo.

7. The agricultural composition of claim 1, wherein $R^5$ is hydrogen or methoxy.

8. The agricultural composition of claim 1, wherein the compound is selected from the group consisting of:

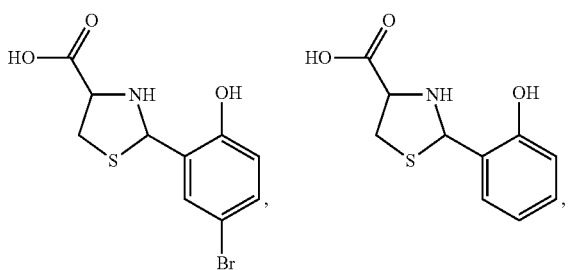

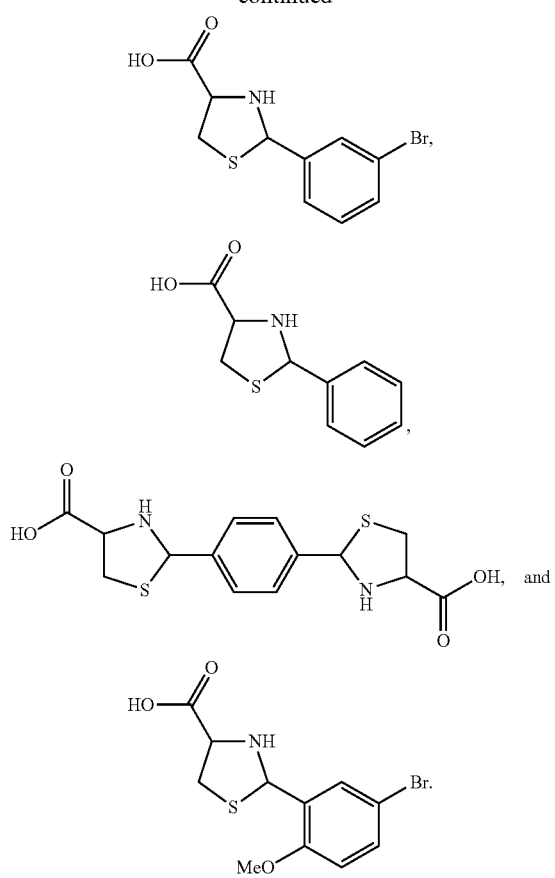

9. The agricultural composition of claim 1, further comprising at least one of an herbicide, an herbicide safener, a surfactant, a fungicide, a pesticide, a nematicide, a plant activator, a synergist, a plant growth regulator, an insect repellant, an acaricide, a molluscicide, or a fertilizer.

10. A method for increasing pathogen resistance in a plant, comprising contacting the plant or part thereof with an effective amount of a compound of Formula I,

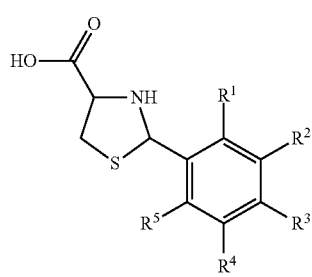

or a salt thereof, wherein:

$R^1$, $R^2$, $R^3$, $R^4$, and $R^5$ are each independently selected from hydrogen, halogen, hydroxyl, alkoxyl, and substituted or unsubstituted heterocycloalkyl, thereby increasing pathogen resistance in the plant compared to pathogen resistance of a control plant not contacted with the compound.

11. The method of claim 10, wherein the compound is selected from the group consisting of:

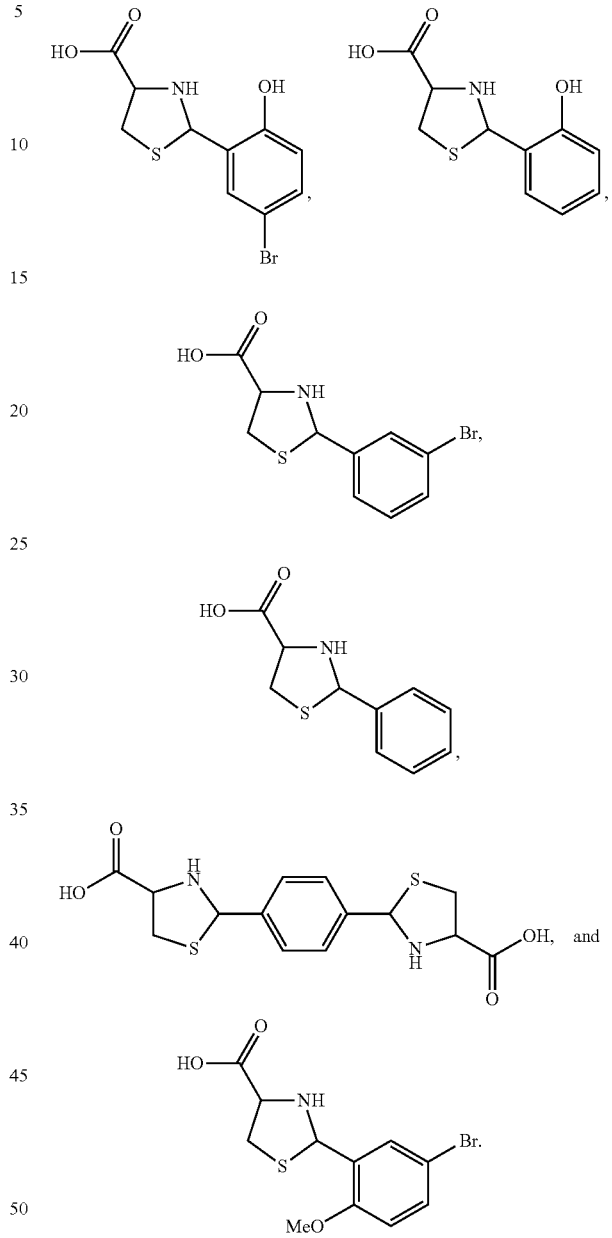

12. The method of claim 10, wherein the compound is applied in solution at a concentration of 10-100 uM.

13. The method of claim 10, wherein the pathogen is present on or in the plant at the time of the contacting step.

14. The method of claim 10, further comprising comparing the amount of pathogen present on the plant before and after the contacting step.

15. The method of claim 10, wherein the compound is applied in combination with at least one of an herbicide, an herbicide safener, a surfactant, a fungicide, a pesticide, a nematicide, a plant activator, a synergist, a plant growth regulator, an insect repellant, an acaricide, a molluscicide, or a fertilizer.

16. A method for increasing growth of a plant or part thereof, comprising
contacting the plant with an effective amount of a compound of Formula I,

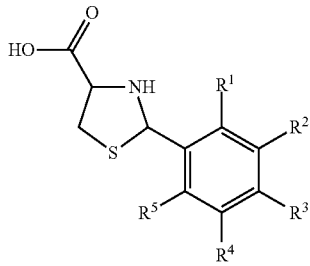

or a salt thereof, wherein:
R¹, R², R³, R⁴, and R⁵ are each independently selected from hydrogen, halogen, hydroxyl, alkoxyl, and substituted or unsubstituted heterocycloalkyl thereby increasing growth of the plant compared to growth of a control plant not contacted with the compound.

17. The method of claim 16, wherein the compound is selected from the group consisting of:

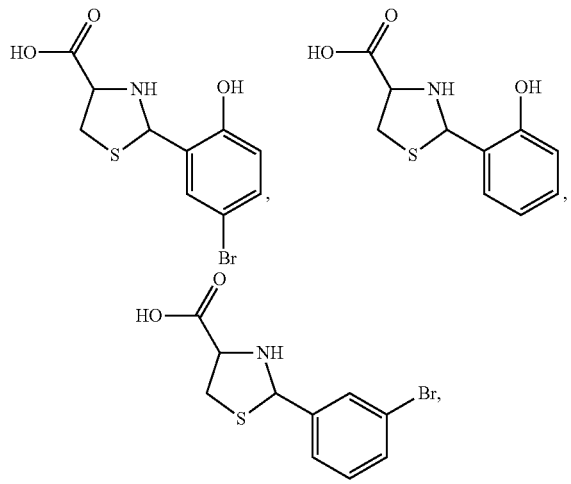

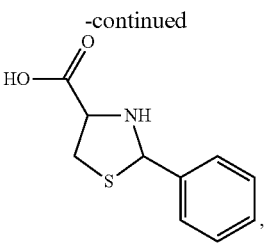

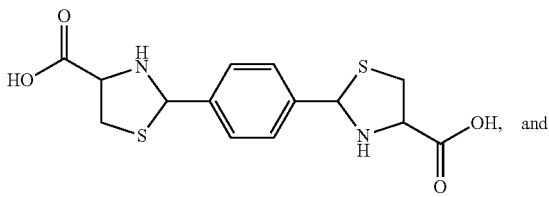

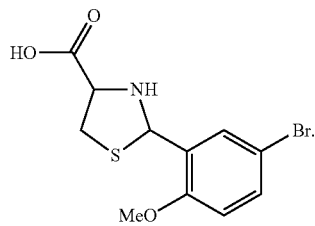

18. The method of claim 16, wherein the compound is applied in solution at a concentration of 0.5-50 uM.

19. The method of claim 16, wherein a pathogen is present on or in the plant at the time of the contacting step.

20. The method of claim 16, wherein the compound is applied in combination with at least one of an herbicide, an herbicide safener, a surfactant, a fungicide, a pesticide, a nematicide, a plant activator, a synergist, a plant growth regulator, an insect repellant, an acaricide, a molluscicide, or a fertilizer.

* * * * *